(12) United States Patent
Schroeder (10) Patent No.: US 7,947,477 B2
(45) Date of Patent: May 24, 2011

(54) EMULSION PCR AND AMPLICON CAPTURE

(75) Inventor: Benjamin Schroeder, San Mateo, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/693,420

(22) Filed: Jan. 25, 2010

(65) Prior Publication Data

US 2010/0129875 A1 May 27, 2010

Related U.S. Application Data

(63) Continuation of application No. 11/763,410, filed on Jun. 14, 2007, now abandoned.

(60) Provisional application No. 60/817,905, filed on Jun. 30, 2006.

(51) Int. Cl.
*C12P 19/34* (2006.01)
*C07H 21/00* (2006.01)

(52) U.S. Cl. .................. 435/91.2; 435/91.21; 435/91.53; 536/24.33; 536/25.32

(58) Field of Classification Search .................. None
See application file for complete search history.

(56) References Cited

U.S. PATENT DOCUMENTS

| | | | |
|---|---|---|---|
| 5,215,899 A | 6/1993 | Dattagupta | |
| 5,871,906 A | 2/1999 | Dyer et al. | |
| 6,808,882 B2 * | 10/2004 | Griffiths et al. | 506/1 |
| 6,818,395 B1 | 11/2004 | Quake et al. | |
| 2005/0037392 A1 | 2/2005 | Griffiths et al. | |
| 2005/0266466 A1 | 12/2005 | Ermantraut et al. | |
| 2008/0076909 A1 | 3/2008 | Schroeder | |

FOREIGN PATENT DOCUMENTS

WO WO-2008/005675 1/2008

OTHER PUBLICATIONS

U.S. Appl. No. 11/377,763, filed Mar. 16, 2006, pp. 1-44.
U.S. Appl. No. 11/763,410, Office Action mailed Jul. 23, 2009, 9 Pgs.
Mayer, G et al., Photoresponsive Compounds, Angew. Chem. Int. Ed., 45, pp. 4901-4921 (2006).
PCTUS0771272 International Preliminary Report on Patentability Issued Jan. 6, 2009, pp. 1-7.
PCTUS0771272 International Search Report mailed May 6, 2008, pp. 1-2.
PCTUS0771272 Written Opinion mailed May 6, 2008, pp. 1-6.

* cited by examiner

*Primary Examiner* — Lawrence E Crane

(57) ABSTRACT

Compositions and methods of use are disclosed for clonally amplifying target polynucleotide sequences in solution and attaching the amplicons to a surface by activation of a masked binding moiety. In an embodiment, the amplicons comprise the masked binding moiety and the surface comprises a binding partner of the binding moiety. Upon activation of the binding moiety, the amplicons bind to the binding partner on the surface. In a non-limiting example, the masked binding moiety is caged biotin or caged fluorescein, while the corresponding binding partner is avidin or an anti-fluorescein antibody.

32 Claims, 3 Drawing Sheets

EMULSION PCR AND AMPLICON CAPTURE

CROSS-REFERENCE TO RELATED APPLICATIONS

This application is a continuation of U.S. patent application Ser. No. 11/763,410 filed Jun. 14, 2007, which is incorporated herein by reference in its entirety. Application Ser. No. 11/763,410 claims a priority benefit under 35 U.S.C. §119(e) from U.S. Provisional Patent Application Ser. No. 60/817,905, filed Jun. 30, 2006, which also is incorporated herein by reference in its entirety.

This application claims benefit under 35 U.S.C. §119(e) to provisional application No. 60/817,905, filed Jun. 30, 2006, the disclosure of which is incorporated herein by reference.

INTRODUCTION

Current methods for clonally amplifying target polynucleotides employ at least one amplification primer attached to a microparticle or another type of surface. The use of an amplification primer attached to a surface facilitates the clonal amplification of large numbers of target polynucleotides in parallel. However, the amplification reaction is encumbered by the use of an amplification primer attached to a surface and is not as efficient in comparison to amplification reactions performed entirely in solution. Therefore, there is a need in the art for compositions and methods that permit the efficient clonal amplification of target polynucleotides.

SUMMARY

These and other features of the present teachings are set forth herein.

This disclosure provides compositions, methods, and kits for the amplification and analysis of polynucleotides. In general, the disclosure provides methods of isolating and clonally amplifying polynucleotides to produce isolated populations of amplicons ("clonal amplicons") and the attachment of clonal amplicons to surfaces. Various methods or techniques can be used to clonally amplify isolated polynucleotides, such as, PCR, including exponential, linear, log-linear, and asymmetric PCR. Therefore, in some embodiments, clonal amplification reactions can include one or more amplification primers.

In some embodiments, the methods comprise isolating a target polynucleotide in various types of reaction vessels, including but not limited to, a well of multiwell plate or a hydrophilic compartment of an inverse emulsion. In some embodiments, target polynucleotides can be clonally amplified entirely in solution using at least one amplification primer that comprises a masked or caged binding moiety. Therefore, disclosed herein are methods and compositions for clonally amplifying target polynucleotides without the use of a primer attached to a surface. However, in some embodiments a surface comprising the binding partner of the binding moiety is not present within the reaction vessel during clonal amplification. In some embodiments, a surface comprising the binding partner can be added to the reaction vessel after amplification. In the various embodiments, the amplicons that are produced can be attached to the surface by unmasking the binding moiety which, as a result, binds to its binding partner. In some embodiments, a masked binding moiety can be a caged biotin and the binding partner can be an anti-biotin antibody or an avidin (e.g., avidin, streptavidin, NEUTRAVIDIN®). In some embodiments, a masked binding moiety can be a caged fluorescein. The caged biotin or fluorescein can be uncaged or activated by various methods such as irradiation with light of an appropriate wavelength.

In some embodiments, a masked binding moiety can be incorporated into amplicons during the amplification reaction. For example, a nucleobase comprising a masked binding moiety can be incorporated into an amplicon by a polymerase during amplification. In some embodiments, a masked binding moiety can be incorporated into a specific site or position of an amplicon. For example, a forward primer can comprise a first non-standard nucleobase that base pairs with a second non-standard nucleobase but does not substantially base pair with A, T, G, C or U. An example of non-standard nucleobases that preferentially base pair include but is not limited to isoC and isoG. In some embodiments, a forward amplification primer can contain at least one isoC or isoG at or near the 5' terminus of a forward amplification primer. IsoC and isoG are known in the art to substantially base pair with each other but not with other nucleobases such as A, T, G, C or U. Therefore, in the example where a forward primer comprises isoC and the triphosphate of isoG is present in the amplification reaction, extension of a reverse amplification primer results in the incorporation of isoG opposite the isoC. In embodiments, wherein the isoG comprises a masked binding moiety, the masked binding moiety is incorporated into the amplicon at the position opposite the isoC.

Clonal amplicons can be analyzed by various methods. In some embodiments, the methods of analysis can be suitable for analyzing various populations of isolated clonal amplicons in parallel. The number of clonal amplicons that can be analyzed in parallel can be determined at the discretion of the practitioner and can include hundreds, thousands, hundreds of thousands, or millions of clonal amplicons. The methods of analysis include but are not limited to detection, single nucleotide polymorphism analysis, sequencing and the like. In various exemplary embodiments, sequencing can be by parallel sequencing, pyrosequencing, fluorescence in situ sequencing, or massively parallel signature sequencing.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION

It is to be understood that both the foregoing general description, including the drawings, and the following detailed description are exemplary and explanatory only and are not restrictive of this disclosure. In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

This disclosure provides compositions, methods, and kits for the analysis of polynucleotides. In general, the disclosure provides methods of isolating and amplifying polynucleotides. "Isolated" as used herein refers to placed or standing alone, discrete, detached, separated from others. "Isolated polynucleotide" as used herein refers to a polynucleotide that is detached or separated from other polynucleotides in a manner and under conditions suitable to yield isolated amplified sequences ("isolated amplicons"). The disclosed methods of isolating and amplifying polynucleotides to yield isolated populations of amplicons can be referred to as "clonal amplification". The methods and techniques employed in the analysis of clonal amplicons can be selected at the discretion of the practitioner and include but are not limited to detection, sequencing, resequencing, quantitation, single-nucleotide polymorphism analysis, and the like.

The methods disclosed herein are suitable for analyzing complex polynucleotides and complex mixtures of polynucleotides. For example, the disclosed methods can be used to sequence an entire genome (e.g., cell, organism, or virus) or a subset of specific polynucleotides sequences. Therefore, in some embodiments, specific polynucleotide sequences of interest can be selected, clonally amplified, and analyzed to the exclusion of other polynucleotide sequences that may be present in a sample.

In some embodiments, a plurality of polynucleotides can be clonally amplified and analyzed in parallel. "Parallel reaction" as used herein refers to a reaction comprising a plurality of discrete regions suitable for performing a plurality of reactions simultaneously. Virtually any number of polynucleotides can be clonally amplified in parallel. For example, in various exemplary embodiments, hundreds, thousands, hundreds of thousands, millions, and even greater numbers of polynucleotides can be analyzed in parallel by the disclosed methods. In various exemplary embodiments the numbers of polynucleotides analyzed in parallel can be at least 2, 100, 500, 1000, 10000, 50000, 100000, 300000, 500000, or 1000000, and even greater.

In some embodiments, limiting dilution can be used to isolate polynucleotides in a manner that is suitable for clonal amplification. For example, a sample comprising a plurality of polynucleotides can be diluted to a concentration such that aliquots of the diluted sample that can be placed into individual reaction vessels (e.g., wells of a multi-well plate) can be predicted to comprise on average >0 and <1 polynucleotide. (U.S. Application No. 20050130173, 20060040297) Therefore, a percentage of reaction vessels can be predicted on a statistical basis (e.g., Poisson distribution) to comprise an isolated polynucleotide suitable for clonal amplification. Determining a dilution suitable for obtaining isolated polynucleotides is within the abilities of the skilled artisan. Factors to be considered include but are not limited to the polynucleotide concentration and the expected number, types, and composition of various polynucleotides that may be present in a sample. In some embodiments, a dilution suitable for obtaining isolated polynucleotides from a sample can be determined empirically. Once isolated within the reaction vessels, polynucleotides can be amplified by various methods as described below to produce clonal amplicons.

In some embodiments, polynucleotide sequences suitable for clonal amplification can be isolated in individual hydrophilic compartment of an inverse emulsion. (U.S. Pat. Nos. 5,616,478, 5,958,698, 6,001,568, 6,432,360, 6,485,944, 6,511,803, 6,440,706, 6,489,103, 6,753,147, 6,753,147, 6,808,882; U.S. Application Nos. 2002090629, 20020119459, 2002120126, 2002120127, 2002127552, 2003124594, 20040185484, 20040253731, 20050037392, 20050042648, 20050064460, 20050079510, 20050164239, 20060068390; WO0109386; WO0109386, WO03106678, WO03044187, WO04069849, WO0407007, WO05003375, WO05010145; Dressman et al., 2003, *Proc. Natl. Acad. Sci. USA* 100(15):8817-22; Mitra et al., 1999, *Nucleic Acids Res.* 27(24):e34; and Shendure et al., 2004, *Nat. Rev. Genet.* 5(5): 335-44, incorporated by reference). "Inverse emulsion", "water-in-oil emulsion" ("W/O") and grammatical equivalents as used herein refer to a colloidal composition comprising a discontinuous hydrophilic phase distributed as discrete compartments in a continuous, hydrophobic phase. As the skilled artisan will appreciate, the volume of the hydrophilic compartments in general are not uniform and their average dimensions can be dependent upon several factors, including but not limited to the composition of the hydrophobic and hydrophilic phases and the method used to prepare the emulsion. In various exemplary embodiments, the mean diameter of hydrophilic compartments can be about 0.5 µm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm to about 500 µm. In various exemplary embodiments, the mean volume of hydrophilic compartments can be about 0.5 µm$^3$ to about 4,000,000 µm$^3$, from about 500 µm$^3$ to about 500,000 µm$^3$, from about 8,000 µm$^3$ to about 200,000 µm$^3$. However, larger and smaller compartments also can be contemplated. Non-limiting examples of factors that can be considered in determining a suitable volume or diameter of a hydrophilic compartment include but are not limited to the amplification conditions, the method of analyzing the clonal amplicons, the molecule weight and composition of the template polynucleotide.

The composition of the continuous and discontinuous phases of an inverse emulsion can be selected at the discretion of the practitioner. In various exemplary embodiments a continuous phase can be can include an oil (e.g., mineral oil, light mineral oil, silicon oil) or a hydrocarbon (e.g., hexane, heptane, octane, nonane, decane, etc.) and the like. The composition of the various phases can be selected to provide a suitable emulsion under the conditions of clonal amplification. "Suitable emulsion" and equivalents refer to an emulsion that does not substantially degrade, collapse or in which the hydrophilic compartments do not substantially coalesce under the clonal amplification conditions. Therefore, in various exemplary embodiments, an emulsion can be suitable for carrying out reactions at varying temperatures (e.g., thermocycling, such as, PCR), and other conditions (e.g., pH, ionic strength, hybridization conditions, etc.), and in the presence of various reaction components (e.g., nucleic acids, proteins, enzymes, catalysts, co-factors, intermediates, products, by-products, labels, microparticles, etc.).

In some embodiments an inverse emulsion can comprise compositions or compounds that modify the inverse emulsion's stability. In some embodiments, such compounds can be amphipathic and therefore comprise hydrophobic and hydrophilic groups. In various exemplary embodiments, the hydrophilic group can be polar, positively charged or negatively charged. The skilled artisan can appreciate that amphipathic compounds, depending on their concentration and the composition of the various phases, can be used to increase or decrease the stability of an inverse emulsion. Examples of amphipathic compounds include but are not limited to proteins, polypeptides, and surfactants, such as, detergents and emulsifiers, all of which can be used alone or in any combination. For example, an amphipathic compound can be a protein or polypeptide (e.g., albumin), lecithin, sodium oleate, glycolic acid ethoxylate oleyl ether, 4-(1-aminoethyl) phenol propoxylate, glycolic acid ethoxylate 4-tert-butylphenyl ether, glycolic acid ethoxylate oleyl ether, sodium dodecyl sulfate, 3-[(3-cholamidopropyl)dimethylammonia]-1-propanesulfonate, n-dodecyl-β-D-maltoside (lauryl-β-D-maltoside), n-octyl-β-D-glucopyranoside, n-octyl-β-D-thioglucopyranoside (OTG), 4-(1,1,3,3-tetramethylbutyl)phenol polymer, N-lauroylsarcosine, polyethylene-block-poly(ethylene glycol), sodium 7-ethyl-2-methyl-4-undecyl sulfate, glycolic acid ethoxylate lauryl ether, Altox® 4912, Tween® 20, Tween® 80, sorbitan monooleate (Span 80), Triton® X-100, Triton® X-114, Brij®-35, Brij®-58, 3-[(3-cholamidopropyl)-dimethylammonio]-1-propane-sulfonate (CHAPS), Nonidet P-40 (NP-40). For further description of these and/or other amphipathic compounds and methods of use in emulsions see, e.g., Becher, *Emulsions: Theory and Practice,* 3rd ed. Oxford University Press 2001 (ISBN 0841234965); Becher (ed.) *Encyclopedia of Emulsion Technology: Basic Theory Vol. I-IV,* Marcel Dekker Inc. 1983 (ISBN: 0824718763), 1985 (ISBN: 0824718771), 1987 (ISBN: 082471878X), 1996 (ISBN: 0824793803); Holmberg, *Surfactants and Polymers in Aqueous Solutions* 2nd ed., John Wiley & Sons 2002 (ISBN: 0471498831); Lissant (ed.), *Emulsions and Emulsion Technology.* Marcel Dekker Inc. 1984 (ISBN: 0824770838); Lissant, *Emulsions and Emulsion Technology (Surfactant Science).* Marcel Dekker Inc. 1974 (ISBN: 0824760972); Lissant (ed.), *Emulsions and Emulsion Technology/Part II* (Surfactant Science, Vol. 6). Marcel Dekker Inc. 1974 (ISBN 0824718925); Lissant, *Emulsions and Emulsion Technology* Marcel Dekker Inc. 1984 (ISBN: 0824790472); *Handbook of Industrial Surfactants* (ISBN 1890595209).

Methods of making inverse emulsions are known in the art and include but are not limited to dropwise addition of an aqueous solution into a stirred hydrophobic solution optionally comprising one or more amphipathic compounds (see, e.g., Becher, *Emulsions: Theory and Practice,* 3rd ed. Oxford University Press 2001 (ISBN 0841234965); Becher (ed.) *Encyclopedia of Emulsion Technology: Basic Theory Vol. I-IV,* Marcel Dekker Inc. 1983 (ISBN: 0824718763), 1985 (ISBN: 0824718771), 1987 (ISBN: 082471878X), 1996 (ISBN: 0824793803); Dressman et al., 2003, *Proc. Natl. Acad. Sci.* USA. 100(15):8817-22 (Epub 2003 Jul. 11); Ghadessey et al., 2001, *Proc. Natl. Acad. Sci.* USA. 98:4552-7; Griffiths et al., 2003, *EMBO* 22:24-35; Lissant (ed.), *Emulsions and Emulsion Technology.* Marcel Dekker Inc. 1984 (ISBN: 0824770838); Lissant, *Emulsions and Emulsion Technology (Surfactant Science).* Marcel Dekker Inc. 1974 (ISBN: 0824760972); Lissant (ed.), *Emulsions and Emulsion Technology/Part II (Surfactant Science,* Vol. 6). Marcel Dekker Inc. 1974 (ISBN 0824718925); Lissant, *Emulsions and Emulsion Technology* Marcel Dekker Inc. 1984 (ISBN: 0824790472); Nakano et al., 2003, *J. Biotechnol.* 102(2):117-24; Tawfik et al., 1998, *Nat. Biotechnol.* 16(7):652-6; U.S. Pat. No. 6,489,103; and WO 2002/22869). Therefore, in some embodiments, polynucleotides and reagents suitable for amplification or analysis can be isolated within hydrophilic compartments by dropwise addition of an aqueous solution comprising the polynucleotides and such reagents into a stirred hydrophobic solution. In some embodiments, the polynucleotide concentration of the aqueous solution can be adjusted such that hydrophilic compartments of the inverse emulsion average from >0 to <1 template polynucleotide per compartment.

In some embodiments, emulsion formation can be monitored by high-resolution ultrasonic spectroscopy in which changes in ultrasonic velocity and attenuation that occur as a function of time are indicative of emulsion formation, as known in the art. In some embodiments, the size (e.g., mean droplet diameter), number, and/or composition of the hydrophilic compartments can be analyzed to sort or remove hydrophilic compartments unsuitable for clonal amplification or analysis. Therefore, in some embodiments, probes (e.g., molecular beacons), primers (e.g., scorpions), labels (fluorescent molecules) and other moieties (e.g., magnetic beads) can be included in the hydrophilic compartments to provide a detectable signal or moiety that can be used to identify hydrophilic compartments of interest. Therefore, methods suitable for sorting hydrophilic compartments include but are not limited to microscopic examination (Vogelstein et al., 1999, *Proc. Natl. Acad. Sci.* USA 96:9236-9241; Dressman et al., 2003, *Proc. Natl. Acad. Sci.* USA. 100(15):8817-22 (Epub 2003 Jul. 11) or laser diffraction (Tawfik et al., 1998, *Nat. Biotechnol.* 16(7):652-6), laser Doppler velocimetry/anemometry ("LDV" or "LDA"), flow cytometry, microflow cytometry, affinity chromatography (e.g., columns and/or pads), exposure to magnetic fields, and the like.

In some embodiments, the aqueous solution comprising the polynucleotides that can be used to form an inverse emulsion also can comprise all of the reagents suitable for clonal amplification, including but not limited to, dNTPs, buffer, salts, polymerase, co-factors, primers, labels, and the like. Therefore, the inverse emulsion can be placed under conditions suitable to clonally amplify the template polynucleotides isolated within the various compartments.

Isolated template polynucleotides can be clonally amplified using the principals and techniques of various methods known in the art. Selecting a method suitable for clonal amplification of isolated polynucleotides is within the abilities of the skilled artisan. Methods suitable for clonal amplification include but are not limited to PCR (see, e.g., U.S. Pat. Nos. 4,683,195, 4,683,202, 4,800,159, 4,965,188, 5,075,216, 5,176,995, 5,338,671, 5,386,022, 5,333,675, 5,340,728, 5,405,774, 5,436,149, 5,512,462, 5,618,703, 5,656,493, 6,037,129, 6,040,166, 6,197,563, 6,300,073, 6,406,891, 6,514,736; EP-A-0200362, EP-A-0201184, U.S. Patent Publication No. 20060057611, Edwards et al. (eds.), 2004, Real-Time PCR: An Essential Guide. Horizon Bioscience Norfolk, UK (ISBN 0-9545232-7-X)), LCR (see, e.g., EP-A-320308 and U.S. Pat. Nos. 5,427,930, 5,516,663, 5,686,272, and 5,869,252), OLA (see, e.g. U.S. Pat. Nos. 4,883,750, 5,242,794, 5,521,065, 5,962,223; Brinson et al., 1997, *Genet. Test.* 1(1):61-8. Erratum in: Iovannisci, 1998, Genet. Test. 2(4): 385; Grossman et al., 1994, *Nucleic Acids Res.* 22(21):4527-34. Erratum in: Iovannisci, 1998, *Nucleic Acids Res.* 26(23): 5539; Iannone et al., 2000, *Cytometry* 39(2):131-40; Nickerson et al., 1990, *Proc. Natl. Acad. Sci.* USA. 87(22): 8923-7), Q-beta amplification (see, e.g. U.S. Pat. Nos. 4,786, 600, 4,957,858, 5,356,774, 5,364,760, 5,503,979, 5,602,001, 5,620,851; "Amplifying Probe Assays with Q-Beta Replicase" Bio/Technology 1989: 7(6), 609-10 (Eng.); Pritchard, 1990, *J. Clin. Lab. Anal.* 4:318), NASBA™ (Burchill et al., 2002, *Br. J. Cancer.* 86(1):102-9; Deiman et al., 2002, *Mol. Biotechnol.* 20(2):163-79; Malek et al. "Nucleic Acid Sequence-Based Amplification (NASBA™)" Ch. 36 In Methods in Molecular Biology, Vol. 28: Protocols for Nucleic Acid Analysis by Nonradioactive Probes, Isaac (ed.) Humana Press, Inc., Totowa, N.J. (1994); Romano et al., 1997, *Immunol. Invest.* 26(1-2):15-28), strand displacement amplification ((SDA) U.S. Pat. Nos. 5,270,184 and 5,455,166; Walker. "Empirical Aspects of Strand Displacement Amplification" In PCR Methods and Applications, 3(1):1-6 Cold Spring Harbor Laboratory Press, Cold Spring Harbor, N.Y. (1993), rolling circle amplification (RCA), transcription, and reverse transcription.

Isolated polynucleotides can be clonally amplified in solution using one or more amplification primers. Thus, the amplification primers are not attached to a surface during amplification. This results in enhanced efficiency and yield of amplification products in comparison to amplification procedures in which one or more primers are attached. In some embodiments, isolated polynucleotides can be clonally amplified in solution using one or more amplification primers in the presence of a surface but the primers are not attached to the surface during amplification. Following amplification in solution, the amplicon can be attached or linked to the surface. In various exemplary embodiments, a surface may have a wide variety of forms, including membranes, slides, plates, micromachined chips, microparticles (e.g., beads) and the like. Surfaces may comprise a wide variety of compositions including, but not limited to, glass, plastic, silicon, alkanethiolate derivatized gold, cellulose, low cross linked and high cross linked polystyrene, silica gel, polyamide, and the like, and can have various shapes and features (e.g., wells, indentations, channels, etc.). Methods of attaching polynucleotides to a surface are known in the art (see, e.g., Beier et al., 1999, *Nucleic Acids Res.* 27(9):1970-1977; Brison et al., 1982, *Molecular and Cellular Biology* 2:578 587; Cheung et al., 1999, *Nat. Genet.* 21(1 Suppl):15-19; Chrisey et al., 1996, *Nucleic Acids Res.* 24(15):3031-3039; Cohen et. al., 1997, *Nucleic Acids Res.* 1997 Feb. 15; 25(4):911-912; Devivar et al., 1999, *Bioorg. Med. Chem. Lett.* 9(9):1239-1242; Herne et al., 1997. *J. Am. Chem. Soc.* 119:8916-8920; Kumar et al., 2000, *Nucleic Acis Res.* 28(14):e71; Lipshutz et al., 1999, *Nat. Genet.* 21(1 Suppl):20-24; Milner et al., 1997, *Nat. Biotechnol.* June; 15(6):537-541; Morozov et al., 1999, *Anal. Chem.* 71(15):3110-3117; Proudnikov et al., 1998, *Anal Biochem.* 259(1):34-41; Rasmussen et al., 1991, *Anal Biochem.* 198(1):138-142; Rogers et al., 1999, *Anal. Biochem.* 266(1): 23-30; Salo et al., 1999, *Bioconjug Chem.* 10(5):815-823; Singh-Gasson et al., 1999, *Nat. Biotechnol.* 17(10):974-978, and Pierce Chemical Company Catalog 1994, pp. 155-200), incorporated herein by reference).

Figure 1:
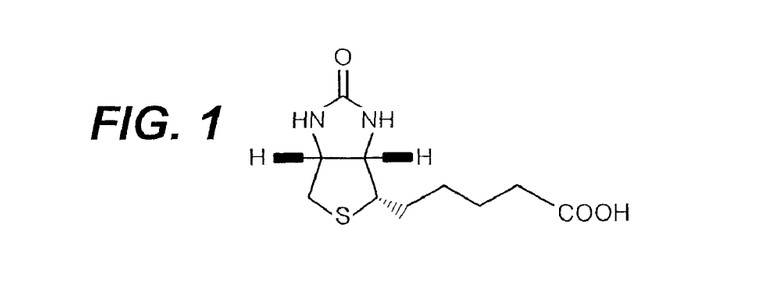
FIG. 1 illustrates the structure of biotin ($C_{10}H_{16}N_2O_3S$).
Figure 2:
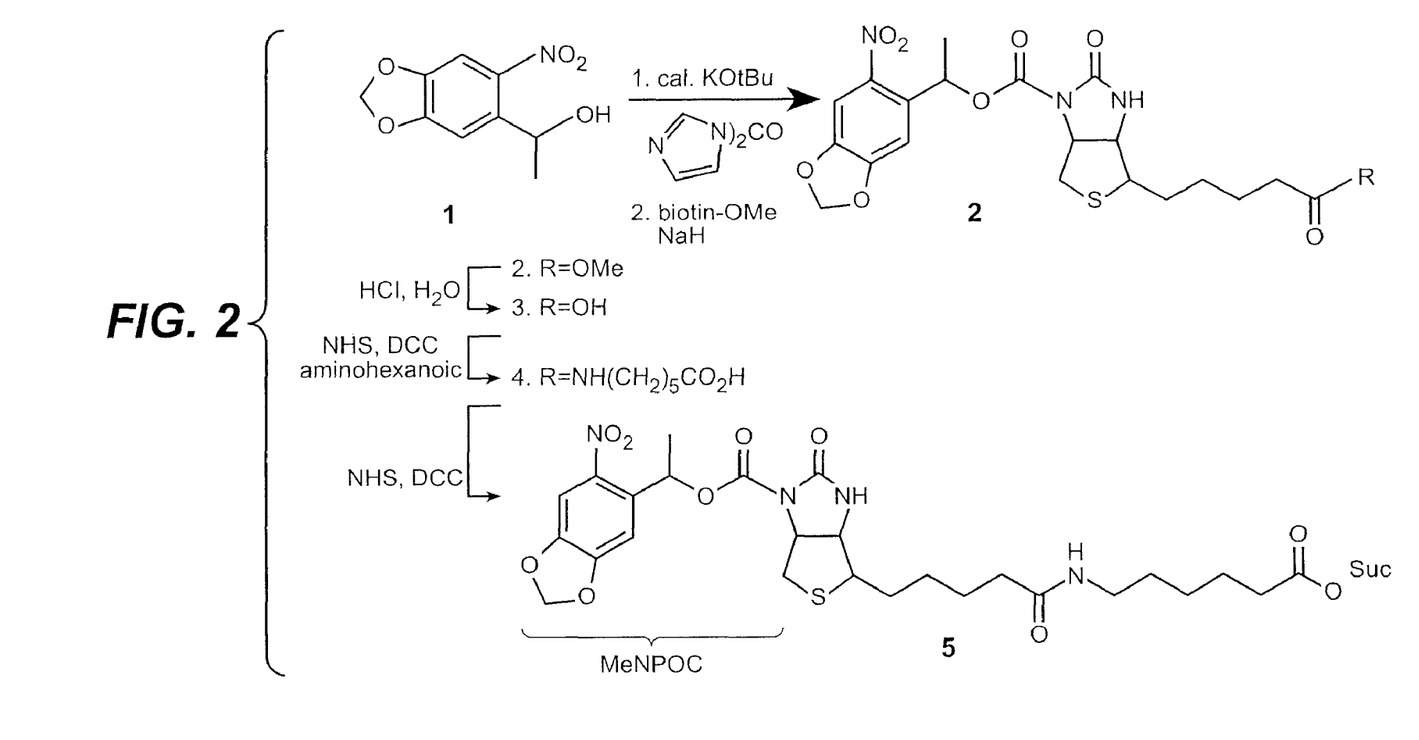
FIG. 2 illustrates an embodiment of the synthesis of a caged biotin. (Pirrung et al. Bioconjug Chem. 1996 May-June; 7(3):317-21; WO0040712).

In some embodiments, an amplicon can be attached to a surface using a "masked binding moiety" which can be referred to as an "activatable capture moiety". Non-limiting examples of a masked binding moiety include a caged binding moieties such as caged biotin (Pirrung et al. Bioconjug Chem. 1996 May-June; 7(3):317-21; WO0040712) and caged fluorescein (5-carboxyfluorescein-bis-(5-carboxymethoxy-2-nitrobenzyl) either, β-alanin-carboxamide, succinimidyl ester (CMNB-caged carbosyfluorescein): Catalog No. C-20050—Invitrogen Corporation, Carlsbad, Calif.). For example, a template polynucleotide which comprises a sequence to be amplified can be isolated as described above in individual reaction vessels, such as, the discontinuous hydrophilic compartments of an inverse emulsion. The hydrophilic compartments include all of the reagents required for amplification including at least one amplification primer that comprises a masked binding moiety. Also included within the hydrophilic droplet can be a surface such as a microparticle comprising a binding partner of an "uncaged" or "activated" binding moiety, such as, an anti-biotin antibody, avidin, streptavidin, NEUTRAVIDIN®, or an anti-fluorescein antibody. As a result of primer extension during amplification, the masked binding moiety is incorporated into the amplicon. Following amplification, the amplicon can irradiated with an appropriate wavelength of light (e.g., ultraviolet light). This causes photochemical cleavage of the caging group which yields "uncaged" or "activated" binding moiety (FIG. 1) which binds its binding partner. As a result, the amplicon becomes attached to the microparticle. A method of synthesizing a caged biotin is illustrated in FIG. 2. Methods of attaching a masked binding moieties, such as, caged biotin or caged fluorescein or to a base, sugar, or phosphate are known in the art.

Figure 3:
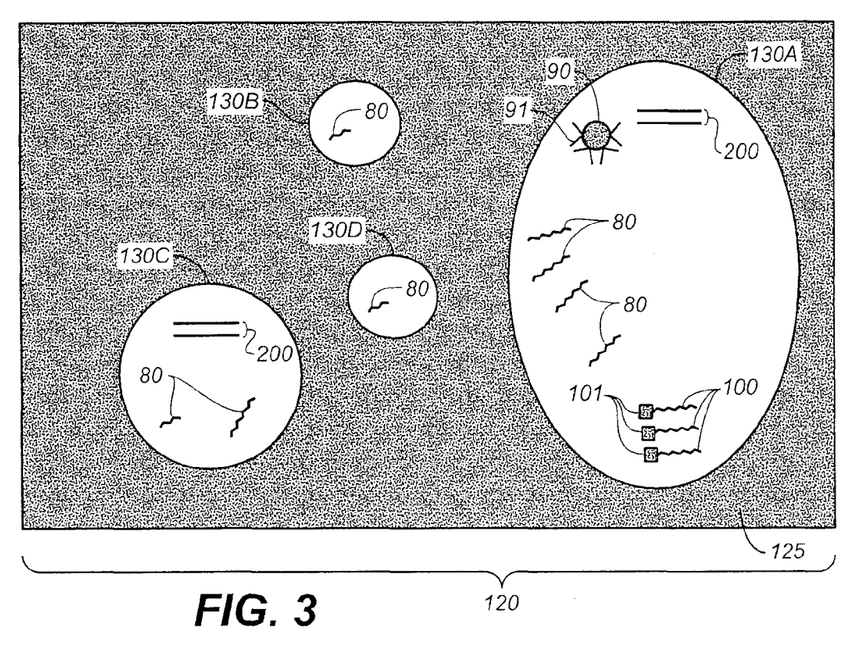
FIG. 3 illustrates an embodiment of an inverse emulsion 120 comprising a hydrophobic phase 125 and a plurality of hydrophilic compartments 130A-D. Hydrophilic compartment 130A contains isolated target polynucleotide 200, multiple copies of reverse primer 80, multiple copies of forward primer 100 comprising caged biotin 101, microparticle 90 comprising streptavidin 91.
Figure 4:
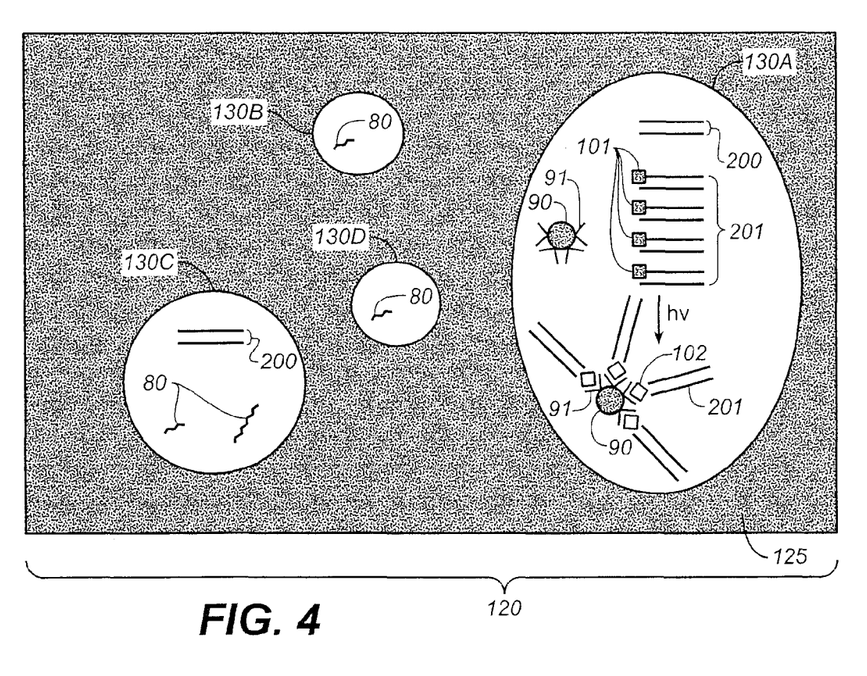
FIG. 4 illustrates an embodiment of an inverse emulsion 120 comprising a hydrophobic phase 125 and a plurality of hydrophilic compartments 130A-D after clonal amplification of polynucleotide 200 by PCR to yield clonal amplicons 201 comprising caged biotin 101. Irradiation (hv (~350 nm)) of the emulsion yields uncaged biotin 102 which binds to streptavidin 91 on microparticle 90.

A non-limiting example of the use of a primer comprising a caged biotin to clonally amplify a target polynucleotide in a hydrophilic compartment of an inverse emulsion is illustrated in FIG. 3 and FIG. 4. In FIG. 3, are shown inverse emulsion 120 comprising hydrophobic phase 125 and a plurality of hydrophilic compartments or droplets 130A-D. Hydrophilic compartment 130A contains isolated polynucleotide 200, multiple copies of reverse primer 80, and multiple copies of forward primer 100 comprising a caged biotin 101. Microparticle 90 contained within the hydrophilic compartment comprises streptavidin 91. Clonal amplification of polynucleotide 200 by PCR will yield an isolated population of double stranded clonal amplicons 201 (FIG. 4) which can be attached to microparticle 91 by irradiation with light (hv) which uncages the biotin 102 rendering it suitable for binding to streptavidin 91.

In some embodiments, clonal amplification can be performed in the absence of microparticles within the hydrophilic compartments of an inverse emulsion. In some embodiments, an inverse emulsion can be disposed upon a surface comprising the binding partner of a masked binding moiety. Therefore, in some embodiments, a hydrophilic compartment can comprise a surface by virtue of being disposed on the surface. The hydrophilic compartments are disposed upon the surface and the target polynucleotide can be clonally amplified. Following clonal amplified the binding moiety can be uncaged to bind its binding partner.

Figure 5:
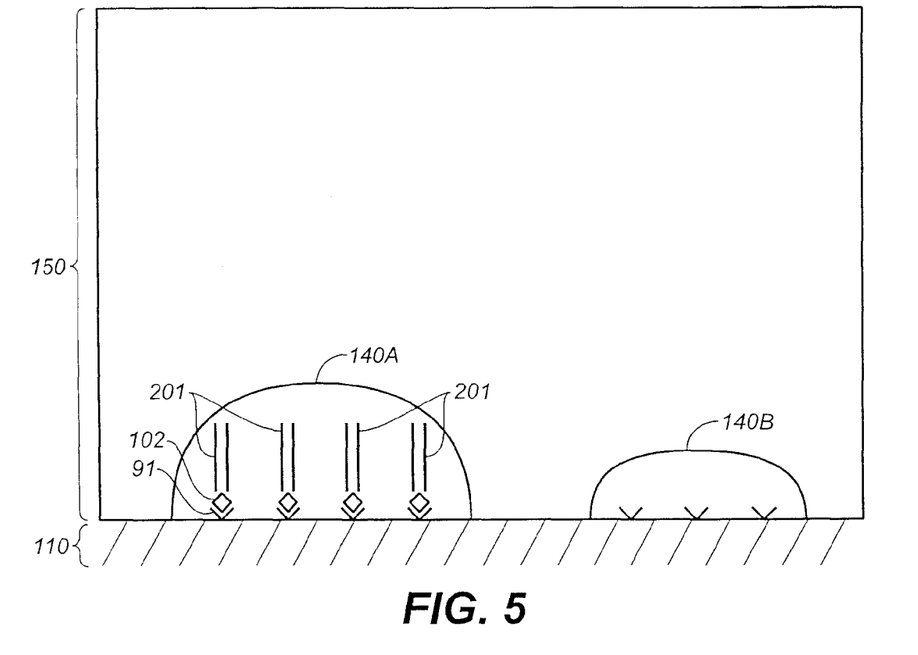
FIG. 5 illustrates an embodiment of an inverse emulsion 150 comprising a plurality of hydrophilic compartments 140A-B disposed upon surface 110 comprising streptavidin 91. Clonal amplicons 201 comprising uncaged biotin 102 are bound to streptavidin 91 after clonal amplification.
Figure 6:
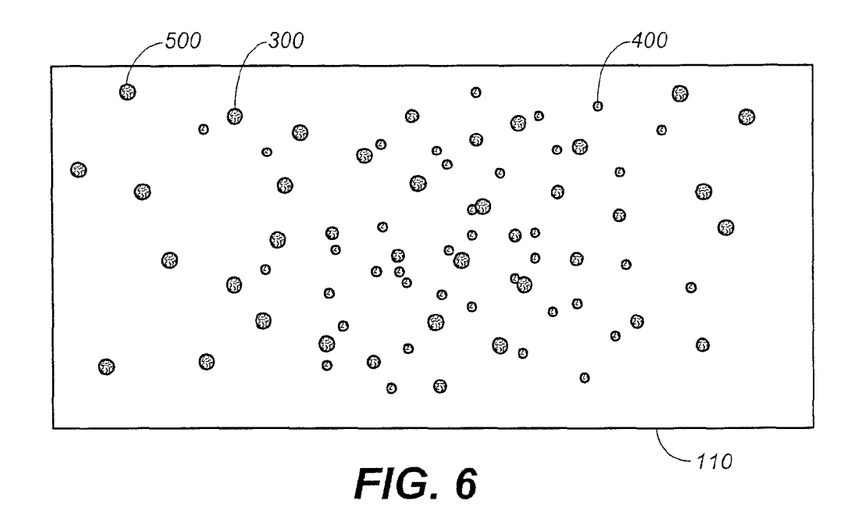
FIG. 6 illustrates an embodiment of clonal amplicons 300, 400, 500 attached to discrete areas of surface 110.

In some embodiments, clonal amplification can be performed in the absence of microparticles within the hydrophilic compartments of an inverse emulsion. For example, target polynucleotides can be clonally amplified in an inverse emulsion to produce amplicons comprising masked binding moiety. Following amplification the inverse emulsion can be disposed upon a surface comprising the binding partner of the binding moiety. After the hydrophilic compartments settle upon the surface, irradiation can uncage the binding moiety and as a result the amplicons bind to the surface. In FIG. 5, are shown an inverse emulsion 150 comprising a plurality of hydrophilic compartments 140A-B disposed upon surface 110. Compartment 140A contains amplicons comprising uncaged biotin bound to streptavidin on surface 110. FIG. 6 illustrates an embodiment in which surface 110 comprises a plurality of regions comprising clonal amplicons 300, 400, 500, and others.

In some embodiments, a nucleobase comprising a masked binding moiety can be incorporated into an amplicon during amplification. In some embodiments, this can be accomplished using nucleobases that specifically base pair with each other but do not substantially base pair with other nucleobases, such as, A, T, G, C or U. For example, a forward amplification primer can contain at least one isoC. In some embodiments, the isoC can be at or near the 5' terminus of a forward amplification primer. IsoC is known in the art to substantially base pair with isoG but not with other nucleobases such as A, T, G, C, or U. Therefore, if the triphosphate of isoG is present in the amplification reaction, extension of a reverse amplification primer results in the incorporation of isoG opposite the isoC. In embodiments, wherein the isoG comprises a masked binding moiety, the masked binding moiety therefore is incorporated into the amplicon. After amplification, the masked binding moiety attached to the isoG can be uncaged resulting in the amplicon becoming attached to a surface comprising a the appropriate binding partner. Non-standard bases, such as isoC and isoG, are described in U.S. Pat. Nos. 5,432,272, 6,001,983, 6,037,120, 6,104,0496, 6,617,106, 6,977,161; U.S. Patent Application Nos. 20040106108, 20060078936; EP1358352, EP1590482, WO0233126 and WO04065550. Other non-standard bases that base pair include but are not limited to 2,4-diamino-5-(β-D-2'-deoxyribofuranosyl)pyrimidine (dĸ) and deoxyxanthosine triphosphate (dX) (Horlacher et al. PNAS USA 1995; 92:6329-6333; Piccirilli et al. Nature 1990; 343:33-37); 2,4-diaminopyrimidine (pyDAD) and xanthine (puADA) (Sismour et al. Nucleic Acids Res. 2004; 32:728-735). The skilled artisan will appreciate that the use of non-standard bases may require the use of modified polymerase to facilitate their efficient incorporation into amplicons.

In some embodiments, the emulsion can be collapsed and the microparticles comprising the clonal amplicons can be collected for analysis. Methods of collapsing an inverse emulsion are known in the art and include but are not limited to modifying the concentration of an amphipathic compound in the emulsion and/or centrifugation. In some embodiments, the double stranded clonal amplicons can be denatured, leaving one strand of the clonal amplicons attached to the microparticles. In some embodiments, the microparticles can be distributed into wells of a multi-well plate and analyzed as disclosed herein.

In some embodiments, analysis of amplicons can be facilitated by separating microparticles with attached amplicons from microparticles that have an insignificant or a less than threshold amount of amplicon attached. This can be accomplished using various techniques, either alone or in any combination. For example, in some embodiments, the amplification reaction can include nucleotide triphosphates that contain a label, such as a fluorescent label. Therefore, incorporation of the fluorescent label into the amplicon and amplicon attachment to a microparticle permits the separation of microparticles based on the degree, amount, or type of fluorescence. In some embodiments, a label that is incorporated into an amplicon can be non-fluorescent, such as, digoxigenin. Therefore, anti-digoxigenin antibody can be use to facilitate enrichment of microparticles with attached amplicons. In some embodiments, a probe that specifically hybridizes to the amplicon but does not hybridize to the amplification primers can be used to facilitate enrichment of microparticles having attached amplicons. In some embodiments, a label incorporated into an amplicon can be a donor or acceptor of a donor/acceptor fluorescent pair. If the microparticle has the corresponding member of the donor/acceptor pair, attachment of the amplicon to the microparticle can result in a fluorescent signal which can be used to enrich for microparticles having attached amplicons. For example, the isoG described above that comprises a caged biotin can also contain a donor of a donor/acceptor pair. When the microparticle has a suitable acceptor, attachment of the amplicon to the microparticle and irradiation with the proper wavelength of light can result in a fluorescent signal.

In some embodiments, amplicon analysis can be facilitated by removal of unused amplification primers. For example, in embodiments that produce double-stranded amplicons, unused amplification primers that are single stranded can be removed using single-strand specific nuclease. In some embodiments, unused amplification primers can be inactivated using one or more sequestering probes that hybridize to the primers thereby rendering them functionally inactivate. In some embodiments, a sequestering probe can comprise a label or a microparticle to facilitate enrichment.

In some embodiments, polynucleotides that can be isolated, clonally amplified, and analyzed by the disclosed methods can be specific regions of a complex polynucleotide (e.g., a chromosome) or selected from complex mixtures of polynucleotides (e.g., a genome; nucleic acid libraries, etc.). Thus, various aspects or characteristics of complex polynucleotides, such as a genome or a cell or organism, can be specifically targeted and analyzed. Non-limiting examples of genomic regions that can be specifically targeted include but are not limited to cis-acting regulatory elements, regions of rearrangement (e.g., antibody and T-cell receptor genes, oncogenes), recombination, insertion (e.g. viral insertion, e.g., retroviral insertion), deletion, gene duplication, transpositional elements, highly-repetitive sequences, specific genes (e.g., genes that encode RNA or protein (e.g., cell cycle regulators, transcription factors, replication/repair proteins, etc.), pseudogenes, transcribed genes (e.g., the transcriptome), genomic regions associated with a disease state (e.g., cancer, cognitive disorders, birth defects, drug addiction, psychiatric disorders, autoimmune disease etc.) can be selectively analyzed by the disclosed methods. In some embodiments, specific regions of a genome can be selected and analyzed at any one or more stages of a cell cycle, or differentiation, or in response to natural (e.g., antigens, cytokines, hormones, etc.) and/or artificial stimuli (e.g., carcinogens, mutagens, pharmaceuticals etc.). Thus, in some embodiments, the methods disclosed herein can be used to selectively determine the expression and/or transcription profile of one or more cells by selectively targeting genomic regions of interest. In various exemplary embodiments, about 1, 5, 10, 15, 20, 25, 30, 35, 40, 45, 50, 55, 60, 65, 70, 76, 80, 85, 90, 95 or about 100% of a genome can be analyzed by the disclosed methods.

In some embodiments, polynucleotides can be selected for clonal amplification by multiplex amplification of polynucleotide sequences. Therefore, in some embodiments, the disclosed methods can comprise multiplex amplification of polynucleotide sequences to produce a heterogeneous mixture of amplicons ("non-clonal amplicons" or "multiplex amplicons"). Once made, the multiplex amplicons can be isolated, clonally amplified, and analyzed.

In various exemplary embodiments, multiplex amplicons can be made by PCR, which can include exponential, linear, asymmetric, and/or log-linear PCR (see, e.g., U.S. Patent Publication No. 20060057611). In some embodiments, multiplex PCR amplification conditions can be designed to reach a plateau. "Plateau" herein refers to the stage of an amplification reaction (e.g., PCR) when synthesis and consequent accumulation of amplicons may terminate even though primers, template, polymerase and dNTPs can be present. This can occur when hybridization of the first and second strands of double-stranded amplicons to each other competes with the hybridization of the amplification primers to the individual amplicon strands. In some embodiments, a plateau can occur when one or more reagents are consumed (see, e.g., Saunders,

*Quantitative Real-Time PCR* 106, 108 (Edwards et al. eds., 2004 (Horizon Bioscience, Norfolk UK, ISBN 0-9545232-7-X)); and Bustin et al., *Analysis of mRNA Expression by Real-Time PCR* 127 (Edwards et al. eds., 2004 (Horizon Bioscience, Norfolk UK, ISBN 0-9545232-7-X))). However, in some embodiments, amplification conditions can be designed to terminate before a reaction would otherwise reach a plateau. In some embodiments, terminating amplification before reaching a plateau can minimize amplification of polynucleotides that are most abundant in a sample. Therefore, in some embodiments, an equivalent number of multiplex amplicons from various polynucleotide can be produced irrespective of the starting copy number of the various polynucleotides. In some embodiments, terminating a PCR reaction before a plateau can be achieved using a limiting and equivalent number of amplification primer pairs for each target polynucleotide to be analyzed (see, e.g., U.S. Patent Publication No. 20060057611).

In some embodiments, multiplex amplicons can be produced by PCR as described in U.S. Patent Application No. 20040175733, incorporated by reference. Therefore, in some embodiments, the conditions of multiplex amplification can include a concentration of thermostable polymerase, such as, AMPLITAQ GOLD™ DNA polymerase (Applied Biosystems, Applera Corp., Foster City, Calif.) from about 2 U/20 µl to about 16 U/20 µl, from about 2 U/20 µl to about 9 U/20 µl, from about 2 U/20 µl to about 6 U/20 µl, from about 7 U/20 µl to about 16 U/20 µl, or from about 2, 3, 4, 5, 6, 7, 8, 9, 10, 11, 12, 13, 14, 15, or 16 U/20 µl reaction volume. In some embodiments, primer extension can be for about 2, 3, 4, 5, 6, 7, 8, 9, 10 min., or even longer. In some embodiments, multiplex amplification primers can be used at concentrations in the range of about 30-900 nM each primer. Different amplification primer pairs may be present at different concentrations within this range or, alternatively, some or all of the multiplex amplification primers may be present at approximately equimolar concentrations within this range. In some embodiments, at least some of the multiplex amplification primers, for example, approximately 10%, 25%, 35%, 50%, 60%, or more, can be present in approximately equimolar concentrations ranging from about 30 nM to about 100 nM each primer. In some embodiments, all of the multiplex amplification primers can be present at approximately equimolar concentrations in the range of about 30 nM to about 100 nM each primer. In some embodiments, all of the amplification primers can be present at concentrations of about 10, 20, 30, 40, 45, 50, 60, 70, 80, 90, 100, 200, 300, 400, 500, 600, 700, 800 or 900 nM each primer. In some embodiments, some or all of the amplification primers can be present in a concentration of about 45 nM each primer. The amplification primer concentrations discussed above can be used regardless of whether the target polynucleotide(s) being amplified are RNA or DNA. In some embodiments, the number of primer pairs can be at least 100, 200, 300, 400, 500, 600, 700, 800, 900, 1000, 2000, 3000, 4000, 5000, 6000, 7000, 8000, 9000, 10000, 15000, 20000, 25000 or up to about 30000. In addition, in embodiments wherein targeted polynucleotides are RNA, the reverse-transcription reaction of a multiplex RT-PCR amplification works well at the stated primer concentrations.

The number of multiplex amplification cycles performed may depend upon, among other factors, the degree of amplification desired, which may depend upon such factors as the amount of polynucleotide to be multiplex amplified and/or the intended method of clonal amplification and analysis. Accordingly, the number of cycles employed can vary for different applications and will be apparent to those of skill in the art. For most applications, multiplex amplification reactions carried out for about 10 amplification cycles can be expected to yield sufficient amplification product even when the sample is of limited quantity (e.g., 1 to a few cells), a polynucleotide of interest is present in very low copy number, and/or is present only as a single copy, regardless of the amount of sample required to perform the analysis. However, more or fewer multiplex amplification cycles may be employed. In some embodiments multiplex amplification can be carried out for as many as 1, 2, 3, 4, 5, 6, 7, 8, 9, 10, 11, 12, 13, 14, 15, 16, 17, 18, 19, 20, or more cycles. In some embodiments, multiplex amplification can be carried out for 2-12 cycles, inclusive, for 5-11 cycles, inclusive, or for up to 14 cycles, inclusive.

In addition to sequences suitable for priming multiplex amplification of polynucleotides, one or more multiplex amplification primers can be designed to introduce sequences into multiplex amplicons that can be used to facilitate isolation, clonal amplification, and analysis. However, the skilled artisan will appreciated that other types of sequences also can be introduced into multiplex amplicons, such as, enhancers, promoters, restriction endonuclease sites, etc. In some embodiments, a sequence introduced into a multiplex amplicon may be a code sequence which may be used as a surrogate or marker for each multiplex amplicon. Therefore, each "code sequence" is substantially unique and can be used to identify or distinguish the polynucleotide comprising the code sequence (see, e.g., U.S. Patent Publication Nos. 20060029954, 20060024714, 20060019289, 20060057611). In some embodiments, a multiplex amplification primer sequence may be shared by at least one other amplicon. For example, in some embodiments, a sequence may be common to each forward amplification primer or each reverse amplification primer. Thus, "forward universal sequence" and "reverse universal sequence" refer to multiplex amplification primer sequences shared by each forward or reverse primer, respectively.

In some embodiments, code, universal, and/or other types of sequences can be added to a polynucleotide or multiplex amplicons using linkers and/or adaptors (Sambrook et al., *Molecular Cloning: A Laboratory Manual* 1.84, 1.88-1.89, 1.98-1.102, 1.160-1.161, 11.20-11.21, 11.51-11.55, 11.102 (3d. ed. Cold Spring Harbor Laboratory Press). For example, in some embodiments, a polynucleotide can be sheared, restriction enzyme digested, or treated with a polymerase or kinase to prepare the termini of a polynucleotide for the addition of linkers and/or adaptors. In some embodiments, sequences, including those described above, can be added to a polynucleotide by homologous recombination using RecA and/or other recombinases (see, e.g., U.S. Pat. Nos. 4,888,274, 5,989,879, 6,090,539, 6,074,853, 6,200,812, 6,391,564, 6,524,856). Determining the number, type, length, and composition of the various sequences and their distribution or commonality among polynucleotides or multiplex amplicons employed, including incorporation of sequences into amplification primers and amplicons derived therefrom are known in the art. (see, e.g., U.S. Pat. Nos. 5,314,809, 5,853,989, 5,882,856, 6,090,552, 6,355,431, 6,617,138, 6,630,329, 6,635,419, 6,670,130, 6,670,161; and Weighardt et al., 1993, *PCR Methods and App.* 3:77, the disclosures of which are incorporated by reference).

As will be appreciated by skilled artisans, polynucleotides suitable for analysis by the disclosed methods may be either DNA (e.g., cDNA, genomic DNA, extrachromosomal DNA (e.g. mitochondrial DNA, plasmid DNA), an amplicon) or RNA (e.g., mRNA, rRNA, tRNA, an in vitro transcript, or genomic RNA (e.g., virion RNA (vRNA)) in nature, and may be derived or obtained from virtually any sample or source (e.g., human, non-human, plant, animal, microorganism etc.), wherein the sample may optionally be scarce or of a limited quantity. For example, the sample may be one or a few cells collected from a crime scene or a small amount of tissue collected via biopsy. In some embodiments, the target polynucleotide may be a synthetic polynucleotide comprising nucleotide analogs or mimics, as described below, produced for purposes, such as, diagnosis, testing, or treatment.

In various non-limiting examples, polynucleotide suitable for analysis may be single or double-stranded, or a combination thereof, linear or circular, a chromosome or a gene or a portion or fragment thereof, a regulatory polynucleotide, a restriction fragment from, for example, a plasmid or chromosomal DNA, genomic DNA, mitochondrial DNA, DNA from a construct or library of constructs (e.g., from a YAC, BAC or PAC library), RNA (e.g., mRNA, rRNA or vRNA) or a cDNA or a cDNA library. As known in the art, a cDNA is a single- or double-stranded DNA produced by reverse transcription of an RNA template. Therefore, some embodiments include a reverse transcriptase and one or more primers suitable for reverse transcribing an RNA template into a cDNA. Reactions, reagents and conditions for carrying out such "RT" reactions are known in the art (see, e.g., Blain et al., 1993, *J. Biol. Chem.* 5:23585-23592; Blain et al., 1995, *J. Virol.* 69:4440-4452; *PCR Essential Techniques* 61-63, 80-81, (Burke, ed., J. Wiley & Sons 1996); Gubler et al., 1983, *Gene* 25:263-269; Gubler, 1987, *Methods Enzymol.*, 152:330-335; Sellner et al., 1994, *J. Virol. Method.* 49:47-58; Okayama et al., 1982, *Mol. Cell. Biol.* 2:161-170; and U.S. Pat. Nos. 5,310,652, 5,322,770, and 6,300,073, these disclosures of which are incorporated herein by reference. In some embodiments, a polynucleotide may include a single polynucleotide (e.g., a chromosome, plasmid) from which one or more different sequences of interest may be optionally selected, clonally amplified, and analyzed.

In some embodiments, clonal amplicons can be analyzed by virtually any method selected at the discretion of the practitioner. Therefore, reactions comprising any one or more steps of probe or primer hybridization, primer extension, labeling, etc. can be used to detect, quantitate, and/or determine the composition of clonal amplicons. For example, in some embodiments, the transcriptome of one or more genomes can be amplified by multiplex PCR, as described above, whereby forward and reverse universal amplicons can be incorporated into each amplicon. In some embodiments, the multiplex amplicons can be isolated, for example, in hydrophilic compartments of an inverse emulsion, and clonally amplified using primers comprising the forward and reverse universal sequences.

In some embodiments, clonal amplicons can be analyzed in a parallel manner. Without being bound by theory, because the clonal amplicons that are produced are isolated as discrete populations, the clonal amplicons can be analyzed in parallel. For example, as shown in FIG. 6, the discrete populations of clonal amplicons can be analyzed in parallel as a result of their attachment to discrete areas of a surface. Therefore, in some embodiments, at least at least 100, 500, 1000, 10000, 50000, 100000, 300000, 500000, or 1000000 populations of clonal amplicons can be analyzed in parallel. The skilled artisan will appreciate that various methods can be suitable for parallel analysis of clonal amplicons. Generally, such methods can produce a discrete detectable signal that can be associated or linked to individual populations of clonal amplicons.

In some embodiments, clonal amplicons can be sequenced using sequencing techniques based on sequencing-by-synthesis techniques. For example, in some embodiments the enzymatic method of Sanger et al. 1977, *Proc. Natl. Acad. Sci.*, 74: 5463-5467, can be employed. The Sanger technique uses controlled synthesis of nucleic acids to generate fragments that terminate at specific points along the sequence of interest. Techniques based on the Sanger method typically begin by annealing a synthetic sequencing primer to a nucleic acid template (e.g., target polynucleotide or amplicon). The primer can be extended in the presence of four dNTPs (i.e., dGTP, dCTP, dATP and dTTP) and small proportion of four 2',3'-ddNTPs that carry a 3'-H atom on the deoxyribose moiety, rather than the conventional 3'-OH group. Incorporation of a ddNTP molecule into the growing DNA chain prevents formation of a phosphodiester bond with the succeeding dNTP, thus, extension of the growing chain can be terminated. The products of the reaction are a nested set of oligonucleotide chains with co-terminal 5' termini and whose lengths are determined by the distance between the 5' terminus of the primer used to initiate DNA synthesis and the sites of ddNTP chain termination. These populations of oligonucleotides can be separated by electrophoresis and the sequence of the template DNA determined (see, e.g., U.S. Pat. Nos. 4,994,372, 5,332,666, 5,498,523, 5,800,996, 5,821,058, 5,863,727, 5,945,526, and 6,258,568; and Sanger et al., 1972, *Proc. Natl. Acad. Sci.* USA, 74: 5463-5467; and Sanger, 1981, *Science*, 214: 1205-1210).

Based on the labeling strategy used to identify the bases, described below, sequencing reactions can be performed in parallel. For example, in some embodiments distinguishable labels can be attached to each ddNTP. Therefore, a single extension/termination reaction can be used which contains the four ddNTPs, each comprising a spectrally resolvable label. Suitable spectrally resolvable labels include but are not limited fluorophores. (see, e.g., U.S. Pat. Nos. 5,821,058, 5,332,666, and 5,945,526.)

In some embodiments, a method of sequencing based on the detection of base incorporation by the release of a pyrophosphate and simultaneous enzymatic nucleotide degradation can be used (see, e.g., U.S. Pat. No. 6,258,568). For example, clonal amplicons can be sequenced using a primer and adding four different dNTPs or ddNTPs subjected to a polymerase reaction. As each dNTP or ddNTP is added to the primer extension product, a pyrophosphate molecule is released. Pyrophosphate release can be detected enzymatically, such as, by the generation of light in a luciferase-luciferin reaction (see, e.g., WO 93/23564 and WO 89/09283). Additionally, a nucleotide degrading enzyme, such as apyrase, can be present during the reaction in order to degrade unincorporated nucleotides (see, e.g., U.S. Pat. No. 6,258,568; hereby incorporated by reference in its entirety). In other embodiments, the reaction can be carried out in the presence of a sequencing primer, polymerase, a nucleotide degrading enzyme, deoxynucleotide triphosphates, and a pyrophosphate detection system comprising ATP sulfurylase and luciferase (see, e.g., U.S. Pat. No. 6,258,568).

In some embodiments, a method of sequencing can be fluorescent in situ sequencing (FISSEQ). In FISSEQ, a primer can be extended by adding a fluorescently-labeled dNTP followed by washing away of unincorporated dNTP. The incorporated dNTP can be detected by fluorescence. At each cycle, the fluorescence from previous cycles can be "bleached" or digitally subtracted. (Mitra et al., 2003, *Analytical Biochemistry* 320:55-65; Zhu et al., 2003, *Science* 301:836-8; U.S. Application Nos. 20020120126, 20020120127, 20020127552, 20030099972, 20030124594, and 20030207265). In some embodiments, a method of sequencing can be hybridization sequencing (see, e.g., Baines et al., 1988, *J. Theor. Biol.* 135(3):303-7; Drmanac et al., *Genomics* 4(2):114-28; Khrapko et al., 1989, *FEBS Lett.* 256(1-2):118-22; Lysov et al., 1988, *Dokl Akad Nauk SSSR.* 303(6):1508-11; Pevzner, 1989, *J. Biomol. Struct. Dyn.* 7(1): 63-73); Southern et al., 1992, *Genomics* 13(4):1008-17).

In some embodiments, clonal amplicons attached to a solid support can be sequenced. For example, clonal amplicons attached to a microparticle produced in a hydrophilic compartment can be collected en masse by breaking the emulsion, distributed into individual wells of a multi-well plate, and sequenced. In some embodiments, clonal amplicons attached to a surface of a slide can be sequenced in a parallel reaction.

In some embodiments, clonal amplicons can be sequenced by massively parallel signature sequencing (MPSS) which comprises two techniques: one for tagging and sorting fragments of DNA for parallel processing, and another for the stepwise sequencing the end of a DNA fragment. MPSS is described in U.S. Pat. Nos. 5,599,675, 5,695,934, 5,714,330, 5,763,175, 5,831,065, 5,863,722, 6,013,445, 6,172,214, 6,511,802; U.S. Patent Application Nos. 20040038283, 20040002104, 20030077615; and International Appl. Nos. PCT/US96/09513, PCT/US97/09472. In some embodiments, MPSS can be carried out by ligating an encoded adaptor to an end of a polynucleotide to be sequenced, the encoded adaptor having a nuclease recognition site of a nuclease whose cleavage site is separate from its recognition site; identifying one or more nucleotides at the end of the fragment by the identity of the encoded adaptor ligated thereto, cleaving the polynucleotide with a nuclease recognizing the nuclease recognition site of the encoded adaptor such that the polynucleotide is shortened by one or more nucleotides; and repeating the steps until the nucleotide sequence of the end of the polynucleotide can be determined. (U.S. Pat. No. 6,511, 802)

A variety of nucleic acid polymerases may be used in the methods described herein. For example, the nucleic acid polymerizing enzyme can be a thermostable polymerase or a thermally degradable polymerase. Suitable thermostable polymerases include, but are not limited to, polymerases isolated from *Thermus aquaticus, Thermus thermophilus, Pyrococcus woesei, Pyrococcus furiosus, Thermococcus litoralis*, and *Thermotoga maritima*. Therefore, in some embodiments, "cycle sequencing" can be performed. Suitable thermodegradable polymerases include, but are not limited to, *E. coli* DNA polymerase I, the Klenow fragment of *E. coli* DNA polymerase I, T4 DNA polymerase, T5 DNA polymerase, T7 DNA polymerase, φ29 DNA polymerase, and Bst polymerase, and others. Examples of other polymerizing enzymes that can be used in the methods described herein include but are not limited to T7, T3, SP6 RNA polymerases and AMV, M-MLV and HIV reverse transcriptases.

Non-limiting examples of commercially available polymerases that can be used in the methods described herein include, but are not limited to, TaqFS®, Kentaq1 (AB Peptide, St. Louis, Mo.), Taquenase (ScienTech Corp., St. Louis, Mo.), ThermoSequenase (Amersham), Bst polymerase, Vent$_R$(exo$^-$) DNA polymerase, Reader™Taq DNA polymerase, VENT™ DNA polymerase (New England Biolabs), DEEP-VENT™ DNA polymerase (New England Biolabs), PFU-Turbo™ DNA polymerase (Stratagene), Tth DNA polymerase, KlenTaq-1 polymerase, SEQUENASE™ 1.0 DNA polymerase (Amersham Biosciences), and SEQUENASE 2.0 DNA polymerase (United States Biochemicals).

The products of sequencing reactions can be analyzed by a wide variety of methods. For example, the products can be separated by a size-dependent process, e.g., gel electrophoresis, capillary electrophoresis (CE: e.g., 3730 DNA Analyzer, 3100-Avant genetic analyser (Applied Biosystems, Foster City, Calif.)) (see, e.g., U.S. Pat. Nos. RE37,941, 5,384,024, 6,372,106, 6,372,484, 6,387,234, 6,387,236, 6,402,918, 6,402,919, 6,432,651, 6,462,816, 6,475,361, 6,476,118, 6,485,626, 6,531,041, 6,544,396, 6,576,105, 6,592,733, 6,596,140, 6,613,212, 6,635,164, and 6,706,162) using various polymers (e.g., separation polymer (e.g., POP-4™ POP-6™, or POP-7™ (Applied Biosystems, Foster City, Calif.), linear polyacrylamide (LPA: Kleparnik et al., 2001, *Electrophoresis* 22(4):783-8; Kotler et al., 2002, *Electrophoresis* 23(17):3062-70; Manabe et al., 1998, *Electrophoresis* 19:2308-2316)), chromatography, thin layer chromatography, or paper chromatography. The separated fragments can be detected, e.g., by laser-induced fluorescence (see, e.g., U.S. Pat. Nos. 5,945,526, 5,863,727, 5,821, 058, 5,800,996, 5,332,666, 5,633,129, and 6,395,486), autoradiography, or chemiluminescence. In some embodiments, the products of the sequencing reaction can be separated using gel electrophoresis and visualized using stains such as ethidium bromide or silver stain. The reaction products can also be analyzed by mass spectrometric methods (see, e.g., U.S. Pat. Nos. 6,225,450 and 5,104,12). In some embodiments, products of the sequencing reaction can be analyzed using microfluidic systems, including but not limited to microcapillary electrophoretic systems and methods (see, e.g., Doherty et al., 2004, *Analytical Chemistry* 76:5249-5256; Ertl et al., 2004, *Analytical Chemistry* 76:3749-3755; Haab et al., 1999, *Analytical Chemistry* 71:5137-5145 (1999); Kheterpal et al., 1999, *Analytical Chemistry* 71:31A-37A; Lagally et al., 2000, *Sensors and Actuators* B 63:138-146; Lagally et al., 2001, *Anal. Chem.* 73:565-570; Lagally et al., 2003, *Genetic Analysis Using a Portable PCR-CE Microsystem*, in *Micro Total Analysis Systems Vol.* 2, Northrup et al. (eds.) pp. 1283-1286; Liu et al., 1999, *Anal. Chem.* 71:566-573; Medintz et al., 2000, *Electrophoresis* 21:2352-2358; Medintz et al., 2001, *Genome Research* 11:413-421; Paegel et al., *Current Opinions in Biotechnology* 14:42-50; Scherer et al., 1999, *Electrophoresis* 20:1508-1517; Shi et al., 1999, *Analytical Chemistry* 71:5354-5361; Wedemayer et al., 2001, *BioTechniques* 30:122-128; U.S. Pat. Nos. 6,787,015, 6,787, 016; U.S. Application Nos. 20020166768, 20020192719, 20020029968, 20030036080, 20030087300, 20030104466, 20040045827, 20040096960; EP1305615; and WO 02/08744).

The various primers (e.g., multiplex amplification, clonal amplification, and/or sequencing), generally, should be sufficiently long to prime template-directed synthesis under the conditions of the reaction. The exact lengths of the primers may depend on many factors, including but not limited to, the desired hybridization temperature between the primers and polynucleotides, the complexity of the different target polynucleotide sequences, the salt concentration, ionic strength, pH and other buffer conditions, and the sequences of the primers and polynucleotides. The ability to select lengths and sequences of primers suitable for particular applications is within the capabilities of ordinarily skilled artisans (see, e.g., Sambrook et al. *Molecular Cloning: A Laboratory Manual* 9.50-9.51, 11.46, 11.50 (2d. ed., Cold Spring Harbor Laboratory Press); Sambrook et al., *Molecular Cloning: A Laboratory Manual* 10.1-10.10 (3d. ed. Cold Spring Harbor Laboratory Press)). In some embodiments, the primers contain from about 15 to about 35 nucleotides that are suitable for hybridizing to a target polynucleotide and form a substrate suitable for DNA synthesis, although the primers may contain more or fewer nucleotides. Shorter primers generally require lower temperatures to form sufficiently stable hybrid complexes with target sequences. The capability of polynucleotides to anneal can be determined by the melting temperature ("$T_m$") of the hybrid complex. $T_m$ is the temperature at which 50% of a polynucleotide strand and its perfect complement form a double-stranded polynucleotide. Therefore, the $T_m$ for a selected polynucleotide varies with factors that influence or affect hybridization. In some embodiments, in which thermocycling occurs, the primers can be designed to have a melting temperature ("$T_m$") in the range of about 60-75° C. Melting temperatures in this range tend to insure that the primers remain annealed or hybridized to the target polynucleotide at the initiation of primer extension. The actual temperature used for a primer extension reaction may depend upon, among other factors, for example, the concentration of the primers. For reactions carried out with a thermostable polymerase such as Taq DNA polymerase, in exemplary embodiments primers can be designed to have a $T_m$ in the range of about 60 to about 78° C. or from about 55 to about 70° C. The melting temperatures of the different primers can be different; however, in an alternative embodiment they should all be approximately the same, i.e., the $T_m$ of each primer, for example, in a parallel reaction can be within a range of about 5° C. or less. The $T_m$s of various primers can be determined empirically utilizing melting techniques that are well-known in the art (see, e.g., Sambrook et al. *Molecular Cloning: A Laboratory Manual* 11.55-11.57 (2d. ed., Cold Spring Harbor Laboratory Press)). Alternatively, the $T_m$ of a primer can be calculated. Numerous references and aids for calculating $T_m$s of primers are available in the art and include, by way of example and not limitation, Baldino et al. *Methods Enzymology.* 168:761-777; Bolton et al., 1962, *Proc. Natl. Acad. Sci.* USA 48:1390; Bresslauer et al., 1986, *Proc. Natl. Acad. Sci. USA* 83:8893-8897; Freier et al., 1986, *Proc. Natl. Acad. Sci.* USA 83:9373-9377; Kierzek et al., *Biochemistry* 25:7840-7846; Montpetit et al., 1992, *J. Virol. Methods* 36:119-128; Osborne, 1991, *CABIOS* 8:83; Rychlik et al., 1990, *Nucleic Acids Res.* 18:6409-6412 (erratum, 1991, Nucleic Acids Res. 19:698); Rychlik. *J. NIH Res.* 6:78; Sambrook et al. *Molecular Cloning: A Laboratory Manual* 9.50-9.51, 11.46-11.49 (2d. ed., Cold Spring Harbor Laboratory Press); Sambrook et al., *Molecular Cloning: A Laboratory Manual* 10.1-10.10 (3d. ed. Cold Spring Harbor Laboratory Press)); SantaLucia, 1998, *Proc. Natl. Acad. Sci.* USA 95:1460-1465; Suggs et al., 1981, In *Developmental Biology Using Purified Genes* (Brown et al., eds.), pp. 683-693, Academic Press; Wetmur, 1991, *Crit. Rev. Biochem. Mol. Biol.* 26:227-259, which disclosures are incorporated by reference. Any of these methods can be used to determine a $T_m$ of a primer.

As the skilled artisan will appreciate, in general, the relative stability and therefore, the $T_m$s, of RNA:RNA, RNA:DNA, and DNA:DNA hybrids having identical sequences for each strand may differ. In general, RNA:RNA hybrids are the most stable (highest relative $T_m$) and DNA:DNA hybrids are the least stable (lowest relative $T_m$). Accordingly, in some embodiments, another factor to consider, in addition to those described above, when designing a primer is the structure of the primer and target polynucleotide. For example, in the embodiment in which an RNA polynucleotide is reverse transcribed to produce a cDNA, the determination of the suitability of a DNA primer for the reverse transcription reaction should include the effect of the RNA polynucleotide on the $T_m$ of the primer. Although the $T_m$s of various hybrids may be determined empirically, as described above, examples of methods of calculating the $T_m$ of various hybrids are found at Sambrook et al. *Molecular Cloning: A Laboratory Manual* 9.51 (2d. ed., Cold Spring Harbor Laboratory Press).

The sequences of primers useful for the disclosed methods are designed to be substantially complementary to regions of the target polynucleotides. By "substantially complementary" herein is meant that the sequences of the primers include enough complementarity to hybridize to the target polynucleotides at the concentration and under the temperature and conditions employed in the reaction and to be extended by the DNA polymerase.

In some embodiments, primers can be a nucleobase polymer. By "nucleobase" is meant naturally occurring and synthetic heterocyclic moieties commonly known to those who utilize nucleic acid or polynucleotide technology or utilize polyamide or peptide nucleic acid technology to generate polymers that can hybridize to polynucleotides in a sequence-specific manner. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobases include those nucleobases disclosed in FIGS. 2(A) and 2(B) of Buchardt et al. (U.S. Pat. No. 6,357,163; WO 92/20702 and WO 92/20703).

The skilled artisan will appreciate that the suitability of any nucleobase used in a primer can depend, at least in part, on the intended use of the primer. For example, a nucleobase suitable for a sequencing primer may not be suitable as a multiplex amplification or clonal amplification primer. This is because particular nucleobases may not provide a suitable template for a polymerase. For example, peptide-nucleic acids (PNAs), described below, do not provide a suitable template for polymerases. Therefore, primers comprising one or more PNAs, are generally, not suitable for exponential amplifications by PCR because DNA synthesis ceases when a thermostable polymerase encounters the PNA in the template strand. However, primers comprising PNA can be suitable for sequencing reactions and amplification reactions that do not require a polymerase to read through the PNA, including but not limited to, linear PCR amplifications. Determining the types of nucleobases suitable for primers employed in the various types of amplification and analysis reactions as disclosed herein is within the abilities of the skilled artisan.

Nucleobases can be linked to other moieties to form nucleosides, nucleotides, and nucleoside/tide analogs. As used herein, "nucleoside" refers to a compound consisting of a purine, deazapurine, or pyrimidine nucleoside base, e.g., adenine, guanine, cytosine, uracil, thymine, 7-deazaadenine, 7-deazaguanosine, that is linked to the anomeric carbon of a pentose sugar at the 1' position, such as a ribose, 2'-deoxyribose, or a 2',3'-di-deoxyribose. When the nucleoside base is purine or 7-deazapurine, the pentose is attached at the 9-position of the purine or deazapurine, and when the nucleoside base is pyrimidine, the pentose is attached at the 1-position of the pyrimidine (see, e.g., Kornberg and Baker, *DNA Replication*, 2nd Ed. (Freeman 1992)). The term "nucleotide" as used herein refers to a phosphate ester of a nucleoside, e.g., a mono-, a di-, or a triphosphate ester, wherein the most common site of esterification is the hydroxyl group attached to the C-5 position of the pentose. "Nucleotide 5'-triphosphate" refers to a nucleotide with a triphosphate ester group at the 5' position. The term "nucleoside/tide" as used herein refers to a set of compounds including both nucleosides and/or nucleotides.

"Nucleobase polymer or oligomer" refers to two or more nucleobases connected by linkages that permit the resultant nucleobase polymer or oligomer to hybridize to a polynucleotide having a complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide or peptide nucleic acids. Nucleobase polymers or oligomers can vary in size from a few nucleobases, from 2 to 40 nucleobases, to several hundred nucleobases, to several thousand nucleobases, or more.

"Polynucleotide or oligonucleotide" refers to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof.

In some embodiments, a nucleobase polymer is an polynucleotide analog or an oligonucleotide analog. By "polynucleotide analog or oligonucleotide analog" is meant nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. Nos. 6,013,785 and 5,696,253 (see also, Dagani, 1995, Chem. & Eng. News 4-5:1153; Dempey et al., 1995, J. Am. Chem. Soc. 117:6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g., Elayadi et al., 2002, Biochemistry 41:9973-9981; Koshkin et al., 1998, J. Am. Chem. Soc. 120:13252-3; Koshkin et al., 1998, Tetrahedron Letters, 39:4381-4384; Jumar et al., 1998, Bioorganic & Medicinal Chemistry Letters 8:2219-2222; Singh and Wengel, 1998, Chem. Commun., 12:1247-1248; WO 00/56746; WO 02/28875; and, WO 01/48190.

In some embodiments, a nucleobase polymer is a polynucleotide mimic or oligonucleotide mimic. "Polynucleotide mimic or oligonucleotide mimic" refers to a nucleobase polymer or oligomer in which one or more of the backbone sugar-phosphate linkages is replaced with a sugar-phosphate analog. Such mimics are capable of hybridizing to complementary polynucleotides or oligonucleotides, or polynucleotide or oligonucleotide analogs or to other polynucleotide or oligonucleotide mimics, and may include backbones comprising one or more of the following linkages: positively charged polyamide backbone with alkylamine side chains as described in U.S. Pat. Nos. 5,786,461, 5,766,855, 5,719,262, 5,539,082 and WO 98/03542 (see also, Haaima et al., 1996, Angewandte Chemie Int'l Ed. in English 35:1939-1942; Lesnick et al., 1997, Nucleotid. 16:1775-1779; D'Costa et al., 1999, Org. Lett. 1:1513-1516; Nielsen, 1999, Curr. Opin. Biotechnol. 10:71-75); uncharged polyamide backbones as described in WO 92/20702 and U.S. Pat. No. 5,539,082; uncharged morpholino-phosphoramidate backbones as described in U.S. Pat. Nos. 5,698,685, 5,470,974, 5,378,841, and 5,185,144 (see also, Wages et al., 1997, BioTechniques 23:1116-1121); peptide-based nucleic acid mimic backbones (see, e.g., U.S. Pat. No. 5,698,685); carbamate backbones (see, e.g., Stirchak and Summerton, 1987, J. Org. Chem. 52:4202); amide backbones (see, e.g., Lebreton, 1994, Synlett. February, 1994:137); methylhydroxylamine backbones (see, e.g., Vasseur et al., 1992, J. Am. Chem. Soc. 114:4006); 3'-thioformacetal backbones (see, e.g., Jones et al., 1993, J. Org. Chem. 58:2983) and sulfamate backbones (see, e.g., U.S. Pat. No. 5,470,967). All of the preceding references are herein incorporated by reference.

"Peptide nucleic acid" or "PNA" refers to poly- or oligonucleotide mimics in which the nucleobases are connected by amino linkages (uncharged polyamide backbone) such as described in any one or more of U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,451,968, 6,441,130, 6,414,112 and 6,403,763; all of which are incorporated herein by reference. The term "peptide nucleic acid" or "PNA" shall also apply to any oligomer or polymer comprising two or more subunits of those polynucleotide mimics described in the following publications: Lagriffoul et al., 1994, Bioorganic & Medicinal Chemistry Letters, 4:1081-1082; Petersen et al., 1996, Bioorganic & Medicinal Chemistry Letters, 6:793-796; Diderichsen et al., 1996, Tett. Lett. 37:475-478; Fujii et al., 1997, Bioorg. Med. Chem. Lett. 7:637-627; Jordan et al., 1997, Bioorg. Med. Chem. Lett. 7:687-690; Krotz et al., 1995, Tett. Lett. 36:6941-6944; Lagriffoul et al., 1994, Bioorg. Med. Chem. Lett. 4:1081-1082; Diederichsen, 1997, Bioorg. Med. Chem. 25 Letters, 7:1743-1746; Lowe et al., 1997, J. Chem. Soc. Perkin Trans. 1, 1:539-546; Lowe et al., 1997, J. Chem. Soc. Perkin Trans. 11:547-554; Lowe et al., 1997, I. Chem. Soc. Perkin Trans. 1 1:555-560; Howarth et al., 1997, I. Org. Chem. 62:5441-5450; Altmann et al., 1997, Bioorg. Med. Chem. Lett., 7:1119-1122; Diederichsen, 1998, Bioorg. Med. Chem. Lett., 8:165-168; Diederichsen et al., 1998, Angew. Chem. mt. Ed., 37:302-305; Cantin et al., 1997, Tett. Lett., 38:4211-4214; Ciapetti et al., 1997, Tetrahedron, 53:1167-1176; Lagriffoule et al., 1997, Chem. Eur. 1. 3:912-919; Kumar et al., 2001, Organic Letters 3(9):1269-1272; and the Peptide-Based Nucleic Acid Mimics (PENAMs) of Shah et al. as disclosed in WO 96/04000.

Some examples of PNAs are those in which the nucleobases are attached to an N-(2-aminoethyl)-glycine backbone, i.e., a peptide-like, amide-linked unit (see, e.g., U.S. Pat. No. 5,719,262; Buchardt et al., 1992, WO 92/20702; Nielsen et al., 1991, Science 254:1497-1500).

In some embodiments, a nucleobase polymer is a chimeric oligonucleotide. By "chimeric oligonucleotide" is meant a nucleobase polymer or oligomer comprising a plurality of different polynucleotides, polynucleotide analogs and polynucleotide mimics. For example a chimeric oligo may comprise a sequence of DNA linked to a sequence of RNA. Other examples of chimeric oligonucleotides include a sequence of DNA linked to a sequence of PNA, and a sequence of RNA linked to a sequence of PNA.

In some embodiments, various components of the disclosed methods, including but not limited to primers, ddNTPs, and the reaction compartments, can comprise a detectable moiety. "Detectable moiety," "detection moiety" or "label" refer to a moiety that renders a molecule to which it is attached detectable or identifiable using known detection systems (e.g., spectroscopic, radioactive, enzymatic, chemical, photochemical, biochemical, immunochemical, chromatographic, physical (e.g., sedimentation, centrifugation, density), electrophoretic, gravimetric, or magnetic systems). Non-limiting examples of labels include quantum dots, isotopic labels (e.g., radioactive or heavy isotopes), magnetic labels; spin labels, electric labels; thermal labels; colored labels (e.g., chromophores), luminescent labels (e.g., fluorescers, chemiluminescers), enzyme labels (e.g., horseradish peroxidase, alkaline phosphatase, luciferase, β-galactosidase) (Ichiki, et al., 1993, *J. Immunol.* 150(12):5408-5417; Nolan, et al., 1988, *Proc. Natl. Acad. Sci.* USA 85(8):2603-2607)), antibody labels, and chemically modifiable labels. In addition, in some embodiments, such labels include components of ligand-binding partner pairs (e.g., antigen-antibody (including single-chain antibodies and antibody fragments, e.g., FAb, F(ab)'$_2$, Fab', Fv, etc. (*Fundamental Immunology* 47-105 (William E. Paul ed., 5$^{th}$ ed., Lippincott Williams & Wilkins 2003)), hormone-receptor binding, neurotransmitter-receptor binding, polymerase-promoter binding, substrate-enzyme binding, inhibitor-enzyme binding (e.g., sulforhodamine-valyl-alanyl-aspartyl-fluoromethylketone (SR-VAD-FMK-caspase(s) binding), allosteric effector-enzyme binding, biotin-streptavidin binding, digoxin-antidigoxin binding, carbohydrate-lectin binding, Annexin V-phosphatidylserine binding (Andree et al., 1990, *J. Biol. Chem.* 265(9): 4923-8; van Heerde et al., 1995, *Thromb. Haemost.* 73(2): 172-9; Tait et al., 1989, *J. Biol. Chem.* 264(14):7944-9), nucleic acid annealing or hybridization, or a molecule that donates or accepts a pair of electrons to form a coordinate covalent bond with the central metal atom of a coordinate complex. In various exemplary embodiments the dissociation constant of the binding ligand can be less than about $10^{-4}$-$10^{-6} M^{-1}$, less than about $10^{-5}$ to $10^{-9} M^{-1}$, or less than about $10^{-7}$-$10^{-9} M^{-1}$.

"Fluorescent label," "fluorescent moiety," and "fluorophore" refer to a molecule that may be detected via its inherent fluorescent properties. Examples of suitable fluorescent labels include, but are not limited to, fluorescein, rhodamine, tetramethylrhodamine, eosin, erythrosin, coumarin, methyl-coumarins, pyrene, Malachite Green, stilbene, Lucifer Yellow, Cascade BlueJ, Texas Red, IAEDANS, EDANS, BODIPY FL, LC Red 640, phycoerythrin, LC Red 705, Oregon green, Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE), FITC, Rhodamine, Texas Red (Pierce, Rockford, Ill.), Cy5, Cy5.5, Cy7 (Amersham Life Science, Pittsburgh, Pa.) and tandem conjugates, such as but not limited to, Cy5PE, Cy5.5PE, Cy7PE, Cy5.5APC, Cy7APC. In some embodiments, suitable fluorescent labels also include, but are not limited to, green fluorescent protein (GFP; Chalfie, et al., 1994, *Science* 263(5148):802-805), EGFP (Clontech Laboratories, Inc., Palo Alto, Calif.), blue fluorescent protein (BFP; Quantum Biotechnologies, Inc. Montreal, Canada; Heim et al, 1996, *Curr. Biol.* 6:178-182; Stauber, 1998, *Biotechniques* 24(3):462-471;), enhanced yellow fluorescent protein (EYFP; Clontech Laboratories, Inc., Palo Alto, Calif.), and renilla (WO 92/15673; WO 95/07463; WO 98/14605; WO 98/26277; WO 99/49019; U.S. Pat. Nos. 5,292,658, 5,418,155, 5,683,888, 5,741,668, 5,777,079, 5,804,387, 5,874,304, 5,876,995, and 5,925,558). Further examples of fluorescent labels are found in Haugland, *Handbook of Fluorescent Probes and Research, 9$^{th}$ Edition*, Molecule Probes, Inc. Eugene, Oreg. (ISBN 0-9710636-O-5).

By "microparticle", "microsphere", "microbead", "bead" and grammatical equivalents herein are meant a small discrete synthetic particle. As known in the art, the composition of beads can vary depending on the type of assay in which they are used and, therefore, selecting a microbead composition is within the abilities of the practitioner. Suitable bead compositions include those used in peptide, nucleic acid and organic synthesis, including, but not limited to, plastics, ceramics, glass, polystyrene, methylstyrene, acrylic polymers, paramagnetic materials (U.S. Pat. Nos. 4,358,388, 4,654,267, 4,774,265, 5,320,944, 5,356,713), thoria sol, carbon graphite, titanium dioxide, latex or cross-linked dextrans such as Sepharose, agarose, cellulose, carboxymethyl cellulose, hydroxyethyl cellulose, proteinaceous polymer, nylon, globulin, DNA, cross-linked micelles and Teflon may all be used (see, e.g., *Microsphere Detection Guide* from Bangs Laboratories, Fishers, Ind.), Beads are also commercially available from, for example, Bio-Rad Laboratories (Richmond, Calif.), LKB (Sweden), Pharmacia (Piscataway, N.J.), IBF (France), Dynal Inc. (Great Neck, N.Y.). In some embodiments, beads may contain a cross-linking agent, such as, but not limited to divinyl benzene, ethylene glycol dimethacrylate, trimethylol propane trimethacrylate, N,N'methylene-bis-acrylamide, adipic acid, sebacic acid, succinic acid, citric acid, 1,2,3,4-butanetetracarboxylic acid, or 1,10 decanedicarboxylic acid or other functionally equivalent agents known in the art. In various exemplary embodiments, beads can be spherical, non-spherical, egg-shaped, irregularly shaped, and the like. The average diameter of a microparticle can be selected at the discretion of the practitioner. However, generally the average diameter of microparticle can range from nanometers (e.g. about 100 nm) to millimeters (e.g. about 1 mm) with beads from about 0.2 μm to about 200 μm being preferred, and from about 0.5 to about 10 μm being particularly preferred, although in some embodiments smaller or larger beads may be used, as described below.

In some embodiments a microparticle can be porous, thus increasing the surface area available for attachment to another molecule, moiety, or compound (e.g., a primer). Thus, microparticles may have additional surface functional groups to facilitate attachment and/or bonding. These groups may include carboxylates, esters, alcohols, carbamides, aldehydes, amines, sulfur oxides, nitrogen oxides, or halides. Methods of attaching another molecule or moiety to a bead are known in the art (see, e.g., U.S. Pat. Nos. 6,268,222, 6,649,414). In some embodiments, a microparticle can further comprise a label.

The compositions and reagents described herein can be packaged into kits. In some embodiments, a kit comprises a reagent for making an inverse emulsion comprising one or more aqueous compartments. In some embodiments, the aqueous compartments can be used in conjunction with one or more reagents from commercially available kits, including, but not limited to, those available from Applied Biosystems (i.e., Big Dye® Terminator Cycle Sequencing Kit), Epicentre (i.e., SequiTherm™ Cycle Sequencing Kit), Amersham (i.e., DYEnamic Direct Dye-Primer Cycle Sequencing Kits), Boehringer Mannheim (i.e., CycleReader™ DNA Sequencing Kit), Bionexus Inc. (i.e., AccuPower DNA Sequencing Kit), and USB cycle sequencing kits (i.e., Thermo Sequenase™ Cycle Sequencing Kit).

In some embodiments, a kit can comprise a primer suitable for multiplex or clonal amplification. In some embodiments, a primer can be attached to a surface, such as, a microparticle and/or a slide and the like. In some embodiments each primer can comprise a target specific sequence and/or a universal sequence. In some embodiments, the microparticles can further comprise various labels, including but not limited to, fluorescent and/or magnetic labels. In some embodiments, a kit can comprise a library of primers or primer pairs. In some embodiments, a kit can comprise one or more reaction compartments comprising reagents suitable for performing a reaction selected at the discretion of a practitioner. For example, in some embodiments, a kit can comprise one or more reaction compartments comprising one more sequencing reagents.

The various components included in the kit are typically contained in separate containers, however, in some embodiments, one or more of the components can be present in the same container. Additionally, kits can comprise any combination of the compositions and reagents described herein. In some embodiments, kits can comprise additional reagents that may be necessary or optional for performing the disclosed methods. Such reagents include, but are not limited to, buffers, molecular size standards, control polynucleotides, and the like.

In this application, the use of the singular includes the plural unless specifically stated otherwise. The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

All literature and similar materials cited in this application, including but not limited to, patents, patent applications, articles, books, and treatises, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

What is claimed is:

1. A method of attaching a polynucleotide to a surface comprising:
   generating a hydrophilic compartment of an inverse emulsion comprising a polynucleotide and a surface,
   wherein said-polynucleotide comprises an isoC or isoG to which a photoactivatable binding moiety and said surface comprises a binding moiety binding partner, and
   activating said binding moiety by exposing said compartment to activating light, which activated binding moiety binds to said binding partner, whereby said polynucleotide is attached to said surface.

2. The method according to claim 1, wherein said binding moiety is a caged biotin.

3. The method according to claim 1, wherein said binding moiety is a caged fluorescein.

4. The method according to claim 1, wherein said polynucleotide comprises isoC to which said binding moiety is attached.

5. The method according to claim 1, wherein said polynucleotide comprises isoG to which said binding moiety is attached.

6. The method according to claim 1, wherein said polynucleotide is a primer.

7. The method according to claim 1, wherein said polynucleotide is an amplicon.

8. The method according to claim 7, wherein said polynucleotide comprises a label.

9. The method according to claim 8, wherein said label is digoxigenin.

10. The method according to claim 1, wherein said binding partner is an antibody.

11. The method according to claim 1, wherein said binding partner is streptavidin.

12. The method according to claim 1, wherein said binding partner is attached to a surface of a bead.

13. The method according to claim 1, wherein:
    said light is UV;
    said photoactivatable binding moiety comprises a caged biotin or caged fluorescein;
    said binding partner is attached to a bead; and
    said polynucleotide comprises a label.

14. A method of attaching an amplicon to a bead comprising:
    (a) producing an amplicon in a hydrophilic compartment of an inverse emulsion comprising a template polynucleotide, a bead having a surface and reagents suitable for polynucleotide amplification, wherein said amplicon comprises an isoC or isoG to which a photoactivatable binding moiety and said surface comprises a binding moiety binding partner; and
    (b) activating said binding moiety by exposing said compartment to activating light, which activated binding moiety binds said binding partner whereby said amplicon is attached to said surface of said bead.

15. The method according to claim 14, wherein said binding moiety is a caged biotin.

16. The method according to claim 14, wherein said binding moiety is a caged fluorescein.

17. The method according to claim 14, wherein said amplicon is double stranded.

18. The method according to claim 14, wherein said amplicon is single-stranded.

19. The method according to claim 14, wherein said amplicon is single and/or doublestranded.

20. The method according to claim 14, wherein said amplicon comprises RNA.

21. The method according to claim 14, wherein said amplicon comprises DNA.

22. The method according to claim 14, wherein said amplicon is produced by polymerase chain reaction ("PCR").

23. The method according to claim 22, wherein said PCR is asymmetric PCR.

24. The method according to claim 22, wherein said PCR is linear PCR.

25. The method according to claim 14, wherein said amplicon is produced by a single nucleotide extension.

26. The method according to claim 14, wherein said amplicon is produced by ligase chain reaction ("LCR").

27. The method according to claim 14, wherein said polynucleotide comprises isoC to which said binding moiety is attached.

28. The method according to claim 14, wherein said polynucleotide comprises isoG to which said binding moiety is attached.

29. The method according to claim 14, wherein said amplicon comprises a label.

30. The method according to claim 29, wherein said label is digoxigenin.

31. The method according to claim 14, wherein said binding partner is an antibody.

32. The method according to claim 14, wherein said binding partner is streptavidin.

* * * * *